United States Patent
Chen et al.

(10) Patent No.: US 9,237,878 B2
(45) Date of Patent: Jan. 19, 2016

(54) GENERATION AND ASSESSMENT OF SHEAR WAVES IN ELASTICITY IMAGING

(71) Applicant: Mayo Foundation for Medical Education and Research, Rochester, MN (US)

(72) Inventors: Shigao Chen, Rochester, MN (US); James F. Greenleaf, Rochester, MN (US); Heng Zhao, Rochester, MN (US); Carolina Amador Carrascal, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 14/027,476

(22) Filed: Sep. 16, 2013

(65) Prior Publication Data

US 2014/0018679 A1    Jan. 16, 2014

Related U.S. Application Data

(63) Continuation-in-part of application No. 13/092,574, filed on Apr. 22, 2011.

(60) Provisional application No. 61/702,420, filed on Sep. 18, 2012.

(51) Int. Cl.
*A61B 8/00* (2006.01)
*A61B 8/08* (2006.01)
*G01S 7/52* (2006.01)

(52) U.S. Cl.
CPC .............. *A61B 8/0858* (2013.01); *A61B 8/085* (2013.01); *A61B 8/48* (2013.01); *A61B 8/485* (2013.01); *G01S 7/52022* (2013.01);

(Continued)

(58) Field of Classification Search
USPC ......................................... 600/438, 407, 437
See application file for complete search history.

(56) References Cited

U.S. PATENT DOCUMENTS 5,810,731 A *  9/1998 Sarvazyan et al. ............ 600/438
7,753,847 B2   7/2010 Greenleaf et al.
(Continued)

OTHER PUBLICATIONS

Bercoff et al (Supersonic Shear Imaging: A new Technique for Soft Tissue Elasticity Mapping, IEEE Transactions on Ultrasonics, Ferroelectrics and Frequency control, vol. 51, No. 4, Apr. 2004.*

(Continued)

*Primary Examiner* — Joel F Brutus
(74) *Attorney, Agent, or Firm* — Yakov Sidorin; Quarles & Brady LLP

(57) ABSTRACT

A method for generation and analysis of shear waves in a subject with an ultrasound system. Multiple short ultrasound push pulses are applied, as a set and optionally more than once, to one or more push origins at the subject to produce first and second shear waves of large amplitudes and desired spatial distributions, which are separated in space and time and which have opposite polarity such that initial movements of the subject tissue, respectively caused by the first and second shear waves, occur in opposite directions. At least one mechanical property of the subject (including that represented by shear wave group velocity, phase velocity, and attenuation of a shear wave) is determined based at least in part on a distance between wavefronts of the first and second shear waves.

18 Claims, 17 Drawing Sheets

(52) U.S. Cl.
CPC .......... *G01S 7/52042* (2013.01); *A61B 8/0825* (2013.01); *A61B 8/483* (2013.01)

(56) References Cited

U.S. PATENT DOCUMENTS 7,785,259 B2    8/2010   Zheng et al.
2010/0222678 A1*  9/2010   Bercoff et al. ................ 600/442

OTHER PUBLICATIONS

Chen et al (Shearwave dispersion ultrasound vibrometry (SDUV) for measuring tissue elasticity and viscosity, IEEE Trans Ultrason Ferroelectr Freq Control. Jan. 2009; 56(1): 55-62.*

Li et al (The acoustic wave sensor and soft lithography technologies for cell biological studies, 2008).*

Banks et al (Modeling of propagating shear waves in biotissue employing an internal variable approach to dissipation, 2007).*

Chen et al, Complex Stiffness Quantification Using Ultrasound Stimulated Vibrometry, IEEE Ultrasonics Symposium, 2003; pp. 941-944.

Hasegawa et al, Improving Accuracy in Estimation of Artery-Wall Displacement by Referring to Center Frequency of RF Echo, IEEE Trans. Ultrason., Ferroelec., Freq. Contr., 2006; 53(1):52-63.

Jensen et al, "Calculation of Pressure Fields from Abitrarily Shaped, Apodized, and Excited Ultrasound Transducers," IEEE Trans. Ultrason., Ferroelec., Freq. Contr., 1992, 39(2):262-267.

Jensen, "Field: A Program for Simulating Ultrasound Systems," Paper presented at the 10th Nordic-Baltic Conference on Biomedical Imaging Published in Medical & Biological Engineering & Computing, pp. 351-353, vol. 34, Supplement 1, Part 1, 1996.

Nightingale, et al., On the Feasibility of Remote Palpation Suing Acoustic Radiation Force, J. Accoust. Soc. Am., 2001, 110(1):625-634.

IEEE Trans. Ultrasonic, Ferroelectrics, and Frequency Control. 58, 1344-54, 2011.

IEEE Transactions on Ultrasonics, Ferroelectrics, and Frequency Control, vol. 51, No. 4, 2004.

* cited by examiner

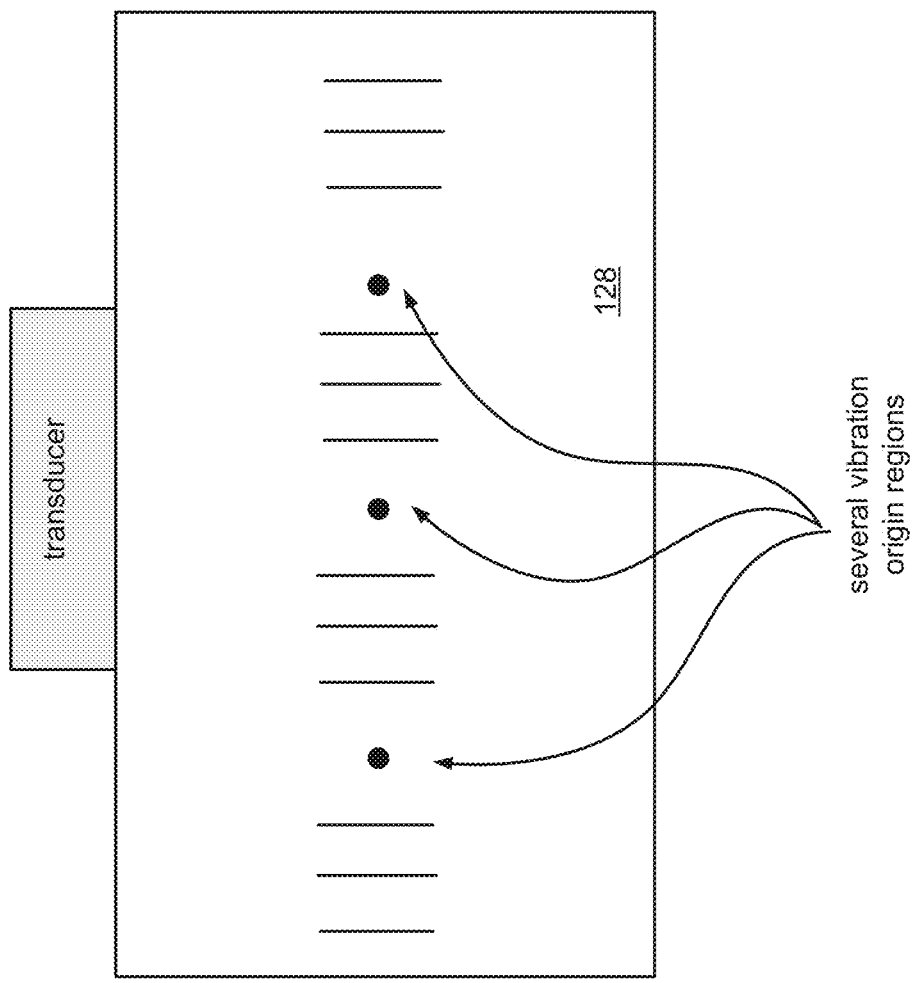

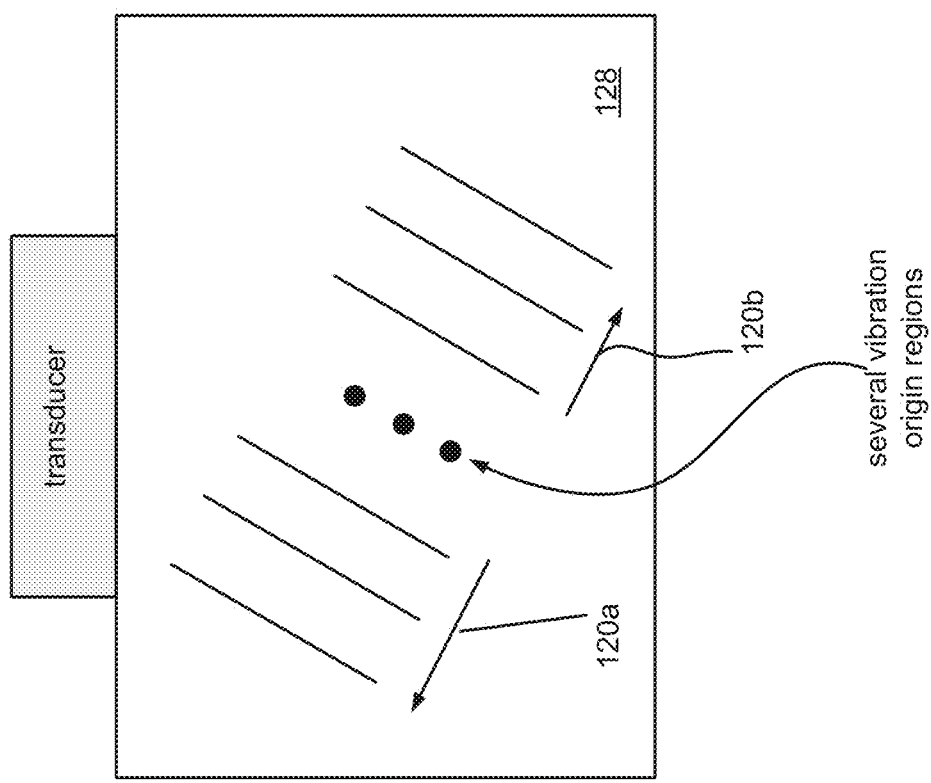

GENERATION AND ASSESSMENT OF SHEAR WAVES IN ELASTICITY IMAGING

CROSS-REFERENCE TO RELATED APPLICATIONS

The present application claims priority from and benefit of the U.S. Provisional Patent Application No. 61/702,420 filed on Sep. 18, 2012 and titled "Generation and Assessment of Shear Waves in Elasticity Imaging". The present application is also a continuation-in-part of the U.S. patent application Ser. No. 13/092,574 filed on Apr. 22, 2011 and titled "Method for Shear Wave Ultrasound Vibrometry with Interleaved Push and Detection Pulses". The disclosure of each of these applications is incorporated by reference herein.

STATEMENT REGARDING FEDERALLY SPONSORED RESEARCH

This invention was made with government support under EB002640 and DK082408 awarded by the National Institutes of Health. The government has certain rights in the invention.

BACKGROUND OF THE INVENTION

The field of the invention is coherent imaging using vibratory energy, such as ultrasound, and, in particular, systems and methods for shear wave based elasticity imaging.

There are a number of modes in which ultrasound can be used to produce images of objects. For example, an ultrasound transmitter may be placed on one side of the object and sound transmitted through the object to an ultrasound receiver placed on the other side of the object. With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("reflection," "backscatter," or "echo" mode).

Acquisition of ultrasound data can be carried out with a number of backscatter methods. In the so-called "A-mode" method, an ultrasound pulse is directed into the object by an ultrasound transducer and the amplitude of the reflected sound is recorded over a period of time. The amplitude of the echo signal is proportional to the scattering strength of the reflectors in the object and the time delay is proportional to the range of the reflectors from the transducer. In the so-called "B-mode" method, the transducer transmits a series of ultrasonic pulses as it is scanned across the object along a single axis of motion. The resulting echo signals are recorded as with the A-mode method and their amplitude is used to modulate the brightness of pixels on a display. The location of the transducer and the time delay of the received echo signals locates the pixels to be illuminated. With the B-mode method, enough data are acquired from which a two-dimensional image of the reflectors can be reconstructed. Rather than physically moving the transducer over the subject to perform a scan it is more common to employ an array of transducer elements and electronically move an ultrasonic beam over a region in the subject.

The ultrasound transducer typically has a number of piezoelectric elements arranged in an array and driven with separate voltages. By controlling the time delay, or phase, and amplitude of the applied voltages, the ultrasonic waves produced by the piezoelectric elements ("transmission mode") combine to produce a net ultrasonic wave focused at a selected point. By controlling the time delay and amplitude of the applied voltages, this focal point can be moved in a plane to scan the subject.

The same principles apply when the transducer is employed to receive the reflected sound ("receiver mode"). That is, the voltages produced at the transducer elements in the array are summed together such that the net signal is indicative of the sound reflected from a single focal point in the subject. As with the transmission mode, this focused reception of the ultrasonic energy is achieved by imparting separate time delays, or phase shifts, and gains to the echo signal received by each transducer array element.

Scanning of an object of interest using a transducer having an array of separately operable elements can be effectuated with electronic methods and systems such as, for example, linear array systems and phased array systems.

A linear array system includes a transducer having a large number of elements typically disposed in a line. A small group of elements are energized to produce an ultrasonic beam that travels away from the transducer, perpendicular to its surface. The group of energized elements is translated along the length of the transducer during the scan to produce a corresponding series of beams that produce echo signals from a two-dimensional region in the subject. To focus each beam that is produced, the pulsing of the inner elements in each energized group is delayed with respect to the pulsing of the outer elements. The time delays determine the depth of focus which can be changed during scanning. The same delay factors are applied when receiving the echo signals to provide dynamic focusing during the receive mode.

A phased array system commonly employs so-called phased array sector scanning ("PASS"). Such a scan is comprised of a series of measurements in which all of the elements of a transducer array are used to transmit a steered ultrasonic beam. The system then switches to receive mode after a short time interval, and the reflected ultrasonic wave is received by all of the transducer elements. Typically, the transmission and reception are steered in the same direction, θ, during each measurement to acquire data from a series of points along a scan line. The receiver is dynamically focused at a succession of ranges, R, along the scan line as the reflected ultrasonic waves are received. A series of measurements are made at successive steering angles, θ, to scan a pie-shaped sector of the subject. The time required to conduct the entire scan is a function of the time required to make each measurement and the number of measurements required to cover the entire region of interest at the desired resolution and signal-to-noise ratio. For example, a total of 128 scan lines may be acquired over a sector spanning 90 degrees, with each scan line being steered in increments of 0.70 degrees.

In the methods described above, multiple ultrasound beams are translated or steered to scan a two-dimensional (2D) area of an object of interest in order to form a 2D B-mode ultrasound image. Assuming that, for example, 100 ultrasound beams are used, the time required for forming such a 2D image is the aggregate of 100 transmit-receive events. If each transmit-receive event lasts 100 microsecond, then the formation of the 2D image takes about 10,000 microseconds. In another B-mode imaging method often referred to as "plane wave imaging", a wave with a substantially planar wavefront is used in the transmission mode. This wave is not focused, typically has a spatial extent comparable to the total width of the aperture of the transducer, and can be formed by applying the transmit voltage to all elements of the transducer without time delay. Echo signals from this "plane wave" transmission are received by each transducer element and stored in corresponding tangible data storage. The stored echo signals from multiple transducer elements are delayed and summed together to reconstruct the ultrasound wave reflected from the object at the location of a given single pixel in the 2D image. This process is repeated for each pixel to obtain the "focused" echoes from all pixels to form an overall 2D image. Different delay parameters are introduced to focus at different pixels. In "plane wave imaging", only one transmit-receive event is required to form a 2D image. Therefore, the image acquisition time for one frame (one 2D image) is small, leading to a higher frame rate as compared to the beam scanning methods described above. Assuming that a transmit-receive event lasts 100 microsecond, for example, a plane wave imaging procedure can have a frame rate of about 10 kHz, whereas the aforementioned example of 100-beam scanning method has a frame rate of 100 Hz.

The same scanning methods may be used to acquire a three-dimensional image of the subject. The transducer in such case is a two-dimensional array of elements which steer a beam throughout a volume of interest or linearly scan a plurality of adjacent two-dimensional slices.

Characterization of mechanical properties of the tissue, particularly the elasticity or tactile hardness of tissue, has important medical applications because these mechanical properties are closely linked to tissue state with respect to pathology. For example, breast cancers are often first detected by the palpation of lesions with abnormal hardness. In another example, a measurement of liver stiffness can be used as a non-invasive alternative for liver fibrosis staging.

The radiation force of ultrasound can be used to generate, remotely, a shear wave within the tissue for noninvasive elasticity imaging. Traditionally, a focused ultrasound beam with long duration (for example, a few hundred microseconds, containing many ultrasound cycles) is used to impart tissue motion at the focus of the ultrasound push beam (referred to as push origin), and a pulse echo ultrasound is used to detect the shear wave propagating outwards from the push origin. The shear wave propagation speed is measured and used to estimate viscoelastic properties of tissue.

The motion of the tissue caused by the push beam is typically very weak (on the order of micrometers), which undermines the reliability of the detection of the shear wave and estimation of tissue viscoelastic properties. The tissue motion increases with amplitude of the push ultrasound beam. However, FDA requirements limit the Mechanical Index (MI) of diagnostic ultrasound to below 1.9 for diagnostic applications in human species. Therefore, the amplitude of the used push beam cannot exceed a certain threshold to avoid exceeding the MI limit.

Another way to increase amplitude of the tissue motion includes increasing the duration of a push pulse. Due to limitations of hardware (for example, due to power droop of transmission circuits) or software (for example, ultrasound output safety watchdogs), current commercial ultrasound scanners may not be equipped to form a push beam with long enough duration to produce a shear wave having sufficiently high amplitude. It would therefore be desirable to provide a method for generating large amplitude shear waves in tissues and do so in a manner that remains within FDA safety limits and that is within the capacity of commercial ultrasound scanners.

Current methods for shear wave detection and shear wave speed estimation are designed to suit traditional ultrasound scanners which image one line from one transmit-receive event. Typically, a shear wave is detected at only a few positions defined along the shear wave propagation path, and detection at each of these positions is repeated at a Pulse Repetition Frequency (PRF) of several kilohertz for tens of milliseconds. Such relatively long detection period may limit the practically use of currently employed methods in responding or detecting rapid changes of tissue elasticity (in a beating heart, for example). In addition, detection of a shear wave signal during the long detection period inevitably exposes the detection process to interference from physiological tissue motion (for example, gross motion of the beating heart). It would therefore be desirable to provide a method for estimation of shear wave speed that requires detection of shear wave in a shorter time period.

SUMMARY OF THE INVENTION

Embodiments of the present invention provide a method for characterizing a subject with an ultrasound system. The method includes applying a set of short ultrasound push pulses to one or more push origins at the subject and detecting, with the ultrasound system, echo energy representing first and second temporally resolved shear waves propagating through the subject from the one or more push origins. The method further includes calculating a mechanical property of the subject using echo data representing the detected echo energy. The first and second shear waves have opposite polarity. In a particular embodiment, the calculating of a mechanical property includes calculating at least one of propagation velocity and attenuation of a shear wave upon its propagation through the subject. Alternatively or in addition, the calculating of a mechanical property may include calculating at least one of a shear storage modulus, a shear loss modulus, and a shear viscosity of the tissue material.

Embodiments of the invention additionally provide a method for characterizing a subject with an ultrasound system, which method includes: (i) detecting ultrasound energy reflected from the subject, the ultrasound energy representing first and second spatially separated shear waves formed in the subject in response to irradiation with an ultrasound beam produced by the ultrasound system, such that the first and second shear waves are characterized by opposite polarity; and (ii) determining spatial distributions of the first and second shear waves at least one moment of time. The method additionally includes calculating a mechanical property using data representing the determined spatial distributions. In one embodiment, the determination of spatial distributions includes determination of a distance between first and second shear wave fronts at at least one moment of time, and the step of calculating includes calculating a group velocity of propagation of a shear wave. (In a specific embodiment, the determination of a distance between the wave fronts includes determining a distance between a front of the first shear wave and a front of the second shear wave. Alternatively or in addition, the determination of spatial distributions may include determining a phase of a shear wave at a given spatial frequency at at least one moment of time, and the step of calculating may include calculating a phase velocity of propagation of a shear wave at a first temporal frequency.) In a related embodiment, the determination of spatial distributions includes determining amplitude of a shear wave at a chosen spatial frequency at at least one moment of time, and the step of calculating includes calculating a parameter representing attenuation of a shear wave at a single temporal frequency. Calculation of a mechanical property may include calculating at least one of a shear storage modulus, a shear loss modulus, and a shear viscosity.

Embodiments of the invention further provide a method for characterizing a double shear wave propagating in a subject with an ultrasound system. Such method includes detecting ultrasound energy reflected from at least two detection points of the subject by irradiating these detection points with ultrasound detection beam emitted by the ultrasound system. The method further includes determining echo data that is indicative of first and second shear waves produced at a push origin region in response to irradiating this vibration origin region with an amplitude-modulated ultrasound push beam emitted by said ultrasound system. The first and second shear waves propagate from the push origin region towards the detection points in question, which points are separated from the push origin region by different respectively-corresponding distances. The first and second shear waves are temporally separated from one another and are configured to cause displacements of a medium of the subject at respectively corresponding velocities having opposite signs. The method further includes determining, from the echo data, at least one of phase and amplitude time-dependent characteristics of said displacement.

Based on the phase and/or amplitude characteristics of the displacement of the medium, a calculation of a mechanical property of the subject can be further performed according to the method of the invention. Either one or both of the amplitude-modulated ultrasound push and detection beams may include temporally-separated pulses. Such temporal separation, in one embodiment, may include a periodic temporal separation. Accordingly, either one or both of the push and detection beams may include pulses characterized by corresponding push and/or detection repetition periods (which may be different or substantially equal). The push and detection pulses may be temporally interleaved. In a specific embodiment, each of the ultrasound detection pulses may be directed to a different motion detection point. The ultrasound detection beam may be focused or unfocused.

Embodiments of the invention further provide a method for characterizing a harmonic motion in a subject with an ultrasound system. Such method includes receiving, with an ultrasound transducer, ultrasound energy reflected from at least one detection point of the subject by irradiating this detection point with ultrasound detection pulses. The method further includes determining, based on detected ultrasound energy, at least one of a phase and an amplitude characteristic of the harmonic motion at a detection point or points in question. The harmonic motion in question is caused in the subject by irradiating a vibration origin region with a sequence of ultrasound push pulses emitted by the ultrasound system such that (i) at least one of the ultrasound push pulses from this sequence precedes at least one of the ultrasound detection pulses, and that (ii) the harmonic motion propagates outwardly from the vibration origin region towards the at least one detection point and is characterized, at the point or points in question, by first and second extrema of displacements of the subject with respect to an equilibrium position. The first and second extrema respectively correspond to displacements of substantially equal amplitudes but opposite in direction and are temporally separated from one another. Each of the ultrasonic push pulses has a corresponding duration that is at least an order of magnitude shorter than duration of said sequence of ultrasound push pulses. A method may additional include calculating a frequency-dependent mechanical property of the subject using the determined phase and/or amplitude of the harmonic motion.

In one implementation, the ultrasound detection pulses are temporally interleaved with the ultrasound push pulses. Alternatively or in addition, an ultrasound push pulse from the sequence of ultrasound push pulses may be substantially focused such as to define the vibration origin region to be substantially coincident with a focal region of the ultrasound push pulse. Furthermore, the ultrasound detection pulses may be temporally periodic and characterized by a detection pulse repetition period.

BRIEF DESCRIPTION OF THE DRAWINGS

FIGS. 7A, 7B, and 7C are diagrams illustrating alternative push schemes for implementation of an embodiment of the invention.

DETAILED DESCRIPTION

The speed and attenuation of the propagating shear wave are closely related to the mechanical properties of tissue. For example, using the Voigt model, the shear wave propagation velocity $c_S$ is related to tissue elasticity $\mu_1$ and viscosity $\mu_2$ by:

$$C_S(\omega_S) = \sqrt{2(\mu_1^2 + \omega_S^2 \mu_2^2)/(\rho(\mu_1 + \sqrt{\mu_1^2 + \omega_S^2 \mu_2^2}))} \qquad \text{Eq. (1),}$$

where $\omega_S$ is the angular frequency of the shear wave and $\rho$ is the tissue density (which, in one case, can be assumed to be about 1000 kg/m$^2$). Eq. (1) can be used to fit the measurement data, representing the frequency-dependent phase velocity of the shear wave, to estimate $\mu 1$ and $\mu_2$. For a tissue having characteristics of a substantially elastic medium, the viscosity $\mu_2$ is substantially zero, and Eq. (1) is simplified to $$C_S = \sqrt{\mu_1/\rho} \qquad \text{Eq. (2)}$$

According to the Voigt model, the attenuation $\alpha_S$ of the shear wave can be expressed as $$\alpha_s(\omega_s) = \sqrt{\frac{\rho \omega_s^2 \left( \sqrt{\mu_1^2 + \omega_s^2 \mu_2^2} - \mu_1 \right)}{2(\mu_1^2 + \omega_s^2 \mu_2^2)}} . \qquad \text{Eq. (3)}$$

Eqs. (1) and (3) can be combined such that $\mu_1$ and $\mu_2$ are calculated from the shear wave speed and attenuation at a single frequency. See, for example, the currently pending U.S. patent application Ser. No. 13/410,780.

Ultrasound-based shear wave measurement techniques typically employ a long duration (hundreds of microseconds) pulse of ultrasound beam to displace tissue in a local spatial region, referred to as the push origin or vibration origin. In the case when the ultrasound push beam is focused, the push origin is associated with the focus of the ultrasound beam. For an unfocused ultrasound push beam, however, the push origin is substantially coextensive with are area of overlap between the beam and the tissue.

Figure 1:
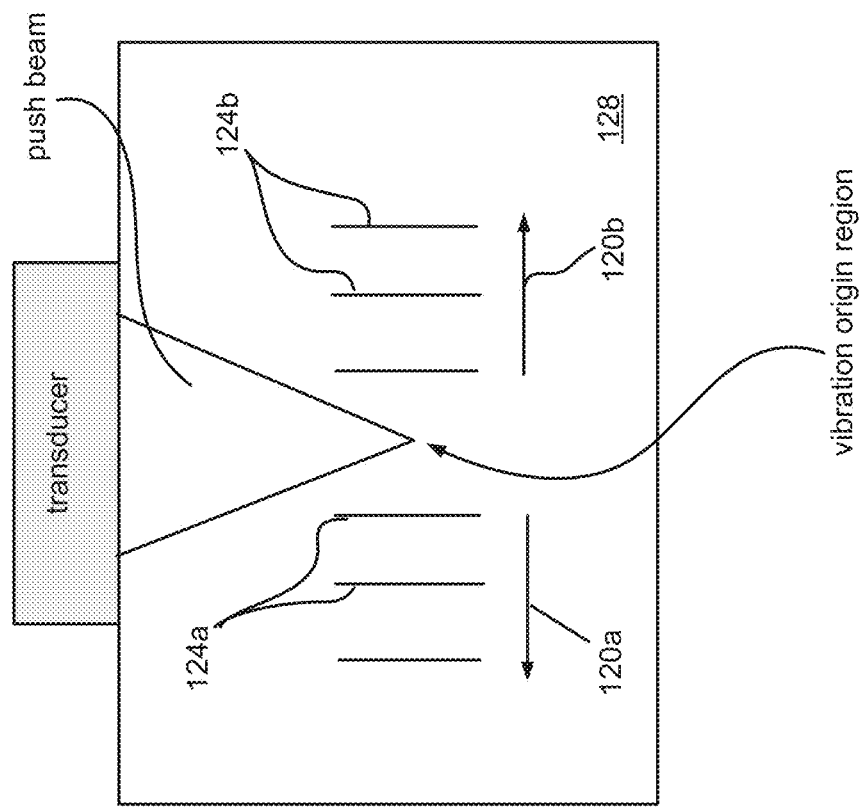
FIG. 1 is a schematic diagram illustrating the application of ultrasound pulses to the tissue to produce shear waves in the tissue.

The applied push-pulse generates tissue motion at the push origin, which propagates in the tissue in a form of a shear wave outwardly from the push origin. A shear wave can be detected at several positions, or motion-detection points, along the propagation path of the wave. As is schematically shown in FIG. 1 with arrows 120a, 120b, as the shear wave 124a, 124b propagates through the tissue 128, tissue particles are displaced away from their respective equilibrium positions. The motion of the particles (characterized by displacement, velocity, and acceleration, for example) occurs in a plane that is substantially perpendicular to the direction of propagation 120a, 120b of the shear wave. The shear wave is detected with pulse-echo ultrasound by irradiating the tissue with multiple detection ultrasound pulses to monitor the shear wave over a period of time.

Figure 2:
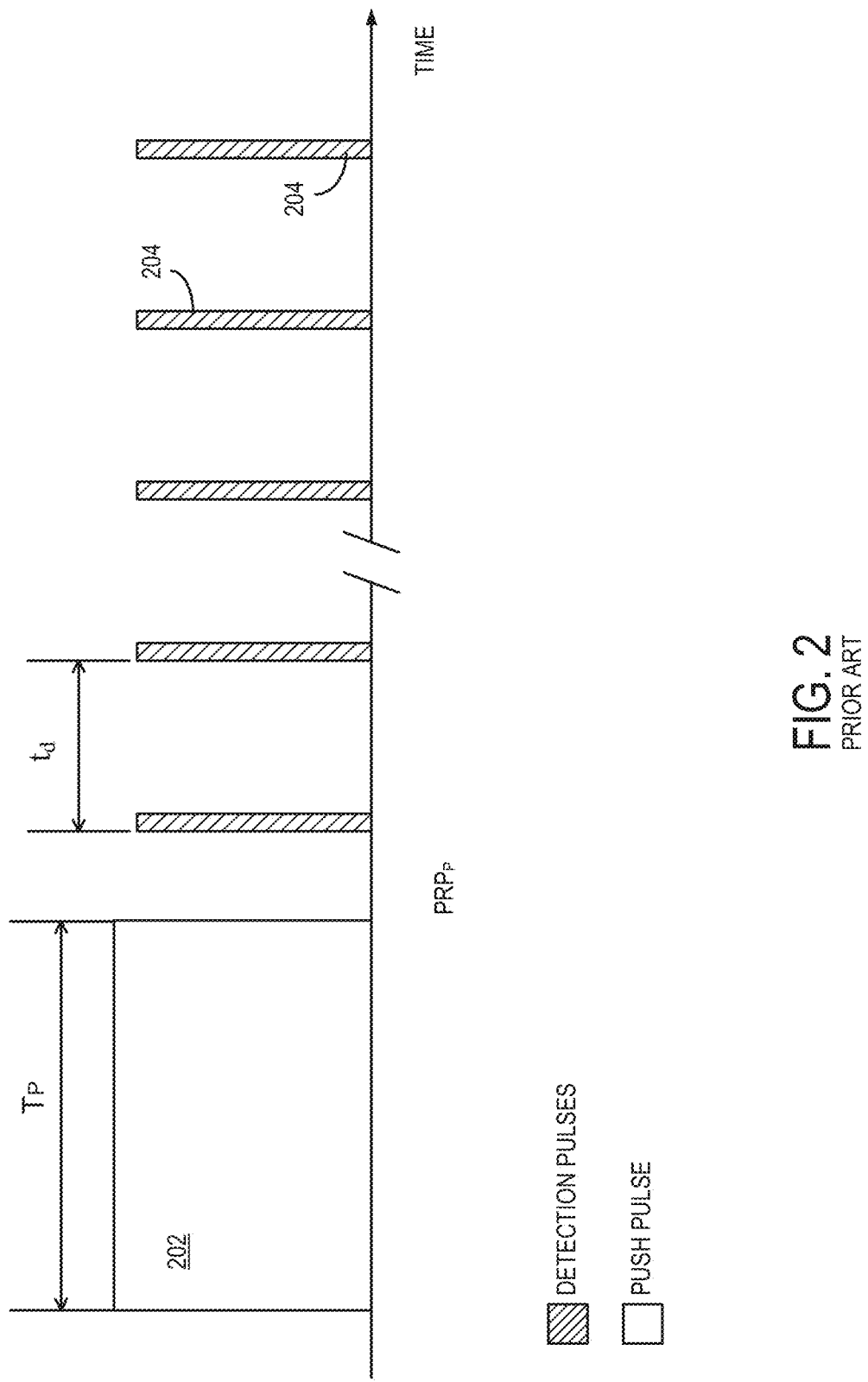
FIG. 2 is a pulse timing diagram indicating the application of ultrasonic push and detection pulses.

An example of a time-diagram showing the push-pulse and push-echo detection pulses is shown in FIG. 2. The push pulse 202 typically has a duration $T_p$ of hundreds of microseconds, and the PRF (Pulse Repetition Frequency) of the detection pulses 204, $PRF_d = 1/t_d$, is typically about a few kilohertz. Detection pulses 204 can be focused where only one A-line is detected from one transmit-receive event (as in traditional ultrasound scanners) or unfocused as in "plane wave imaging" (where the entire 2D area under the ultrasound transducer can be detected for one transmit-receive event).

Referring again to FIG. 1, a shear wave motion is typically detected at several locations along the shear wave propagation path. At each detection location, a multiplicity of transmit-receive events are used to follow tissue motion through time. The tissue motion at each detection location has a peak indicating the arrival of the shear wave front to that detection location. The "time-to-peak" (i.e., the time delay of the peak appearance) is determined by the distance between the detection location and the push origin and the shear wave propagation speed of the tissue. The slope of time-to-peak versus detection position can be used to calculate the shear wave group velocity. Tissue elasticity parameters can then be determined from Eq. (2).

The shear wave phase velocity can also be estimated from time records of the tissue motion detected at several locations along the propagation path. In one example, referred to as "phase regression", Fast Fourier Transform is applied to the time-record of the tissue motion at a detection point. Then the phase of the shear wave at a chosen frequency (for example, at 100 Hz) can be obtained from the spectrum of the time-record. This process can be repeated for other detection locations. The shear wave phase changes linearly with the detection location. The shear wave propagation velocity at the chosen frequency can be calculated from the slope of the phase-position plot and the shear wave frequency. The whole process can be repeated to estimate phase velocity values at other frequencies, and from those values, to determine $\mu_1$ and $\mu_2$ through a rheology model such as the Voigt model referred to in Eq. (1).

Figure 3A:
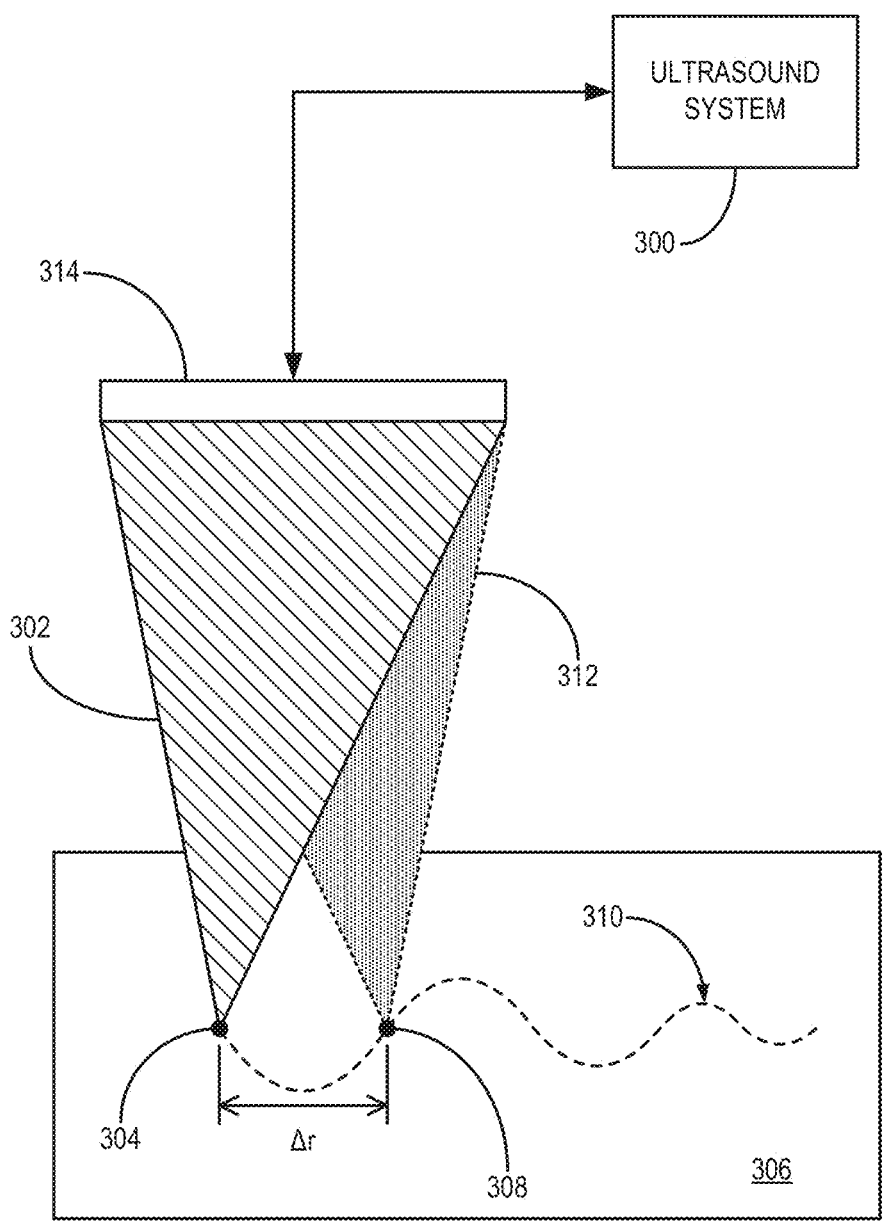
FIG. 3A is block diagram of a shear wave measurement system that employs the present invention.

Referring to FIG. 3A, an exemplary shear wave measurement system includes an ultrasonic transducer 314 that is operable to produce focused ultrasound beams. In particular, the transducer 314, such as a linear array transducer, transmits a beam of ultrasonic pulses 302 to a push origin 304 in the tissue of interest 306 to impart motion in subject tissue 306. Then focus of the transducer may be electronically steered to a motion detection point 308 at a distance, $\Delta r$, from the push origin 304 and shear wave motion 310 at that point is detected by applying interrogating ultrasonic detection pulses 312 at that point. Under the direction of a digital controller of the ultrasound system 300 (which controls the transmission and reception of signals), detection of shear wave motion 310 at different locations can be achieved.

Figure 3B:
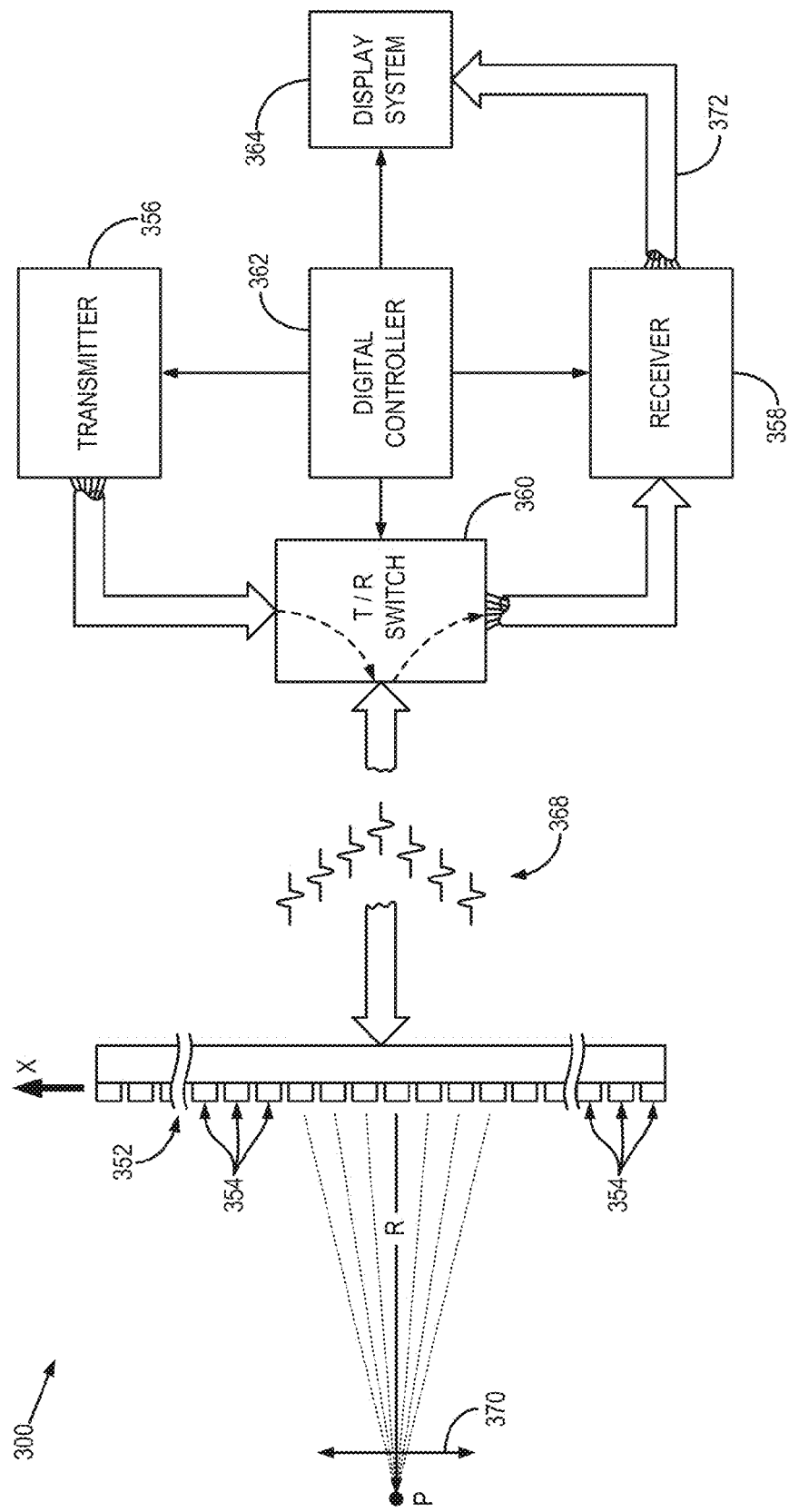
FIG. 3B is a block diagram of an ultrasound system used in the system of FIG. 3A.

Referring particularly now to FIG. 3B, an ultrasonic imaging system 300, which forms a part of the SDUV system of FIG. 3A, includes a transducer array 352 containing a plurality of separately driven elements 354 that each produce a burst of ultrasonic energy when energized by a pulse produced by a transmitter 356. The ultrasonic energy reflected back to the transducer array 352 from the tissue of interest is converted to an electrical signal by each transducer element 354 and applied separately to a receiver 358 through a set of switches 360. The transmitter 356, receiver 358, and the switches 360 are operated under the control of a digital controller 362 responsive to the commands input by the human operator. A complete scan is performed by acquiring a series of echoes in which the switches 360 are set to their transmit position, the transmitter 356 is gated on momentarily to energize each transducer element 354, the switches 360 are then set to their receive position, and the subsequent echo signals produced by each transducer element 354 are applied to the receiver 358. The separate echo signals from each transducer element 354 are combined in the receiver 358 to produce a single echo signal which is employed to produce a line in an image on a display system 364.

The transmitter 356 drives the transducer array 352 such that an ultrasonic beam is produced which is directed substantially perpendicular to its front surface. To focus this beam at a range, R, from the transducer 352 a subgroup of the elements 354 are energized to produce the beam, and the pulsing of the inner elements in this subgroup 354 are delayed relative to the outer elements of 354 as shown at 368. A beam focused at point P results from the interference of the small separate wavelets produced by the subgroup elements. The time delays determine the depth of focus, or range R, and this is typically changed during a scan when a two-dimensional image is to be produced. The same time delay pattern is used when receiving the echo signals resulting in dynamic focusing of the echo signals received by the subgroup of elements 354. In this manner a single scan line in the image is formed.

To generate the next scan line, the subgroup of elements to be energized are shifted one element position along the transducer length and another scan line is required. As indicated by the arrow 370, the focal point, P, of the ultrasonic beam is thus shifted along the length of the transducer 352 by repeatedly shifting the location of the energized subgroup of elements 354.

Figure 3C:
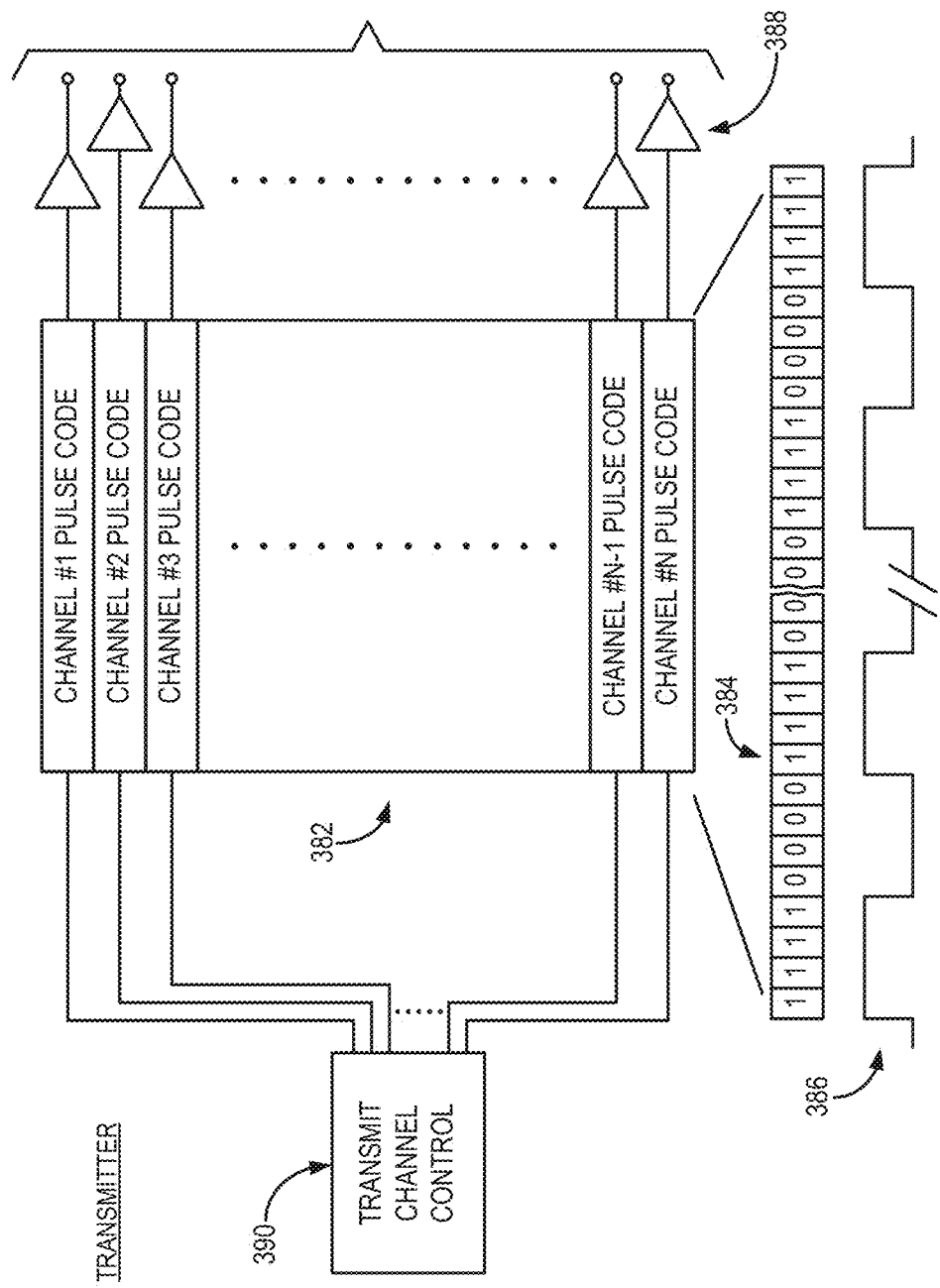
FIG. 3C is a block diagram of a transmitter which forms part of the ultrasound system of FIG. 3A.

Referring now to FIG. 3C, the transmitter 356 includes a set of channel pulse code memories which are indicated collectively at 382. Each pulse code memory 382 stores a bit pattern 384 determining the frequency of the ultrasonic pulse 386 that is to be produced. This bit pattern is read out of each pulse code memory 382 by a master clock and applied to a driver 388 which amplifies the signal to a power level suitable for driving the transducer 352. In the example shown in FIG. 3C, the bit pattern is a sequence of four "1" bits alternated with four "0" bits to produce a 5 megahertz ("MHz") ultrasonic pulse 386. The transducer elements 354 to which these ultrasonic pulses 386 are applied respond by producing ultrasonic energy.

As indicated above, to steer the transmitted beam of the ultrasonic energy in the desired manner, the pulses 386 for each of the channels must be produced and delayed by the proper amount. These delays are provided by a transmit control 390 which receives control signals from the digital controller 362. When the control signal is received, the transmit control 390 gates a clock signal through to the first transmit channel 382. At each successive delay time interval thereafter, the clock signal is gated through to the next channel pulse code memory 382 until all the channels to be energized are producing their ultrasonic pulses 386. Each transmit channel 382 is reset after its entire bit pattern 384 has been transmitted and the transmitter 356 then waits for the next control signal from the digital controller 362. Referring again to FIG. 3B, by operating the transmitter 356 in the above-described manner, the ultrasonic energy can be focused at the focal point, P. This focal point can be steered electronically with the appropriate changes to the timing delays provided by the transmit control 390. The term "focal point," as referred to herein, includes not only a single point object in the usual sense, but also a general region-of-interest to which ultrasound energy is delivered in a substantially focused manner.

Examples of the receiving portion of the ultrasound system 300 of FIG. 3A are described in a co-pending co-assigned U.S. patent application Ser. No. 13/092,574 filed on Apr. 22, 2011, the entire disclosure of which is incorporated by reference herein in its entirety.

For "plane wave imaging", the detection pulse 312 in FIG. 3A includes a plane wave. This can be achieved by pulsing all elements of the transducer 352 without phase delay among them. Echo signals from the plane wave transmission are received by each transducer element and stored in digital memory. The stored echo signals from multiple transducer elements are delayed and summed together to reconstruct the ultrasound reflected from tissue at one location of the tissue illuminated by the plane wave ultrasound pulse. This delay and sum process is repeated to obtain the "focused" echoes from other locations to form a 2D image. Different delay rules are applied to focus at different locations.

Echoes from the same tissue region obtained from two transmit-receive events separate in time can be used to calculate tissue motion from that region between the two transmit-receive events. This can be achieved with many methods such as cross-correlation, auto-correlation, or computations from the Fourier spectrum of the echo signal. In general, pulse echo ultrasound can be used to detect shear waves produced in tissue, and used to calculate shear wave attenuation or velocity for estimation of mechanical properties.

However, the amplitude of the tissue motion caused by the ultrasound push beam is typically rather small (on the order of micrometers), making the detection of shear wave and thus estimation of tissue viscoelastic properties susceptible to noise interference. One way to increase tissue motion is to increase amplitude of the push ultrasound. The FDA limits the Mechanical Index (MI) of diagnostic ultrasound to below 1.9 for diagnostic applications in humans. Therefore, the amplitude of the push beam has to remain sufficiently low to avoid exceeding the MI limit. Increase of the amplitude of the tissue motion can also be achieved by increasing the push pulse duration. However, the currently used commercial ultrasound systems are typically designed to transmit short ultrasound pulse and therefore cannot sustain very long transmission due to power droop of the transmit circuits. In addition, some ultrasound scanners may have built-in software safeguards that limit the upper bound of transmission duration. As a result, currently employed commercial ultrasound scanners are not necessarily configured to provide a continuous push beam with a duration that is long enough to produce a shear wave with high amplitude.

It has been discovered by these inventors that this problem is addressed by substituting a single, long-duration push-pulse with a sequence of short push-pulses. In such a case, the amplitude of the vibratory motion induced in a subject is significantly increased while remaining within the safety limits set by the FDA for intensity of the applied push-pulses.

The idea of the invention stems from the realization that the above-mentioned problem is addressed by substituting a single, long-duration push-pulse with a sequence of short push-pulses. In such a case, the pulses are short in duration and separated in time, leading to a low duty cycle and lower power consumption, and therefore will not cause power droop (drop of transmit voltage). The time intervals between these short push beams are small (typically less than 2 milliseconds each) such that tissue displaced by the previous push pulse in a sequence does not have time to relax and return to its original position. This will ensure that the motion due to all push beams (with output parameters below the FDA safety limits for diagnostic use in human) build up to a larger amplitude for more reliable shear wave detection. In other words, the reaction of the tissue at the push origin is similar to that the tissue would have in response to a long aggregate push pulse beginning with the first short push pulse and ending with the last short push pulse.

In addition, the application of a sequence of short push beams can be applied to multiple push origins and in many cycles to produce shear waves with desired characteristics. For example, the sequence of short push pulses can be focused, in order, at three locations A, B, C at the tissue according to the following time sequence: A, B, C, A, B, C, A, B, C, A, B, C, A, B, C, A, B, C and so on. Assuming the time between immediately sequential push pulses is $\Delta t$, each of the three location will experience a push-pulse every $3\Delta t$. Shear waves produced at A, B, and C will interfere to produce a combined shear wave. The combined shear wave be enhanced in amplitude and steered in propagation direction, by appropriately selecting the spatial locations A, B, and C.

It was furthermore discovered that, when the parameters of the short push-pulses in the sequence and those of the sequence itself are appropriately and non-obviously chosen, the detection of the tissue motion formed in the tissue at the already-mentioned increased amplitude benefits from another, unexpected advantage of having two shear waves produced in the subject as a result of irradiation of the tissue with a single sequence of the short push-pulses. In particular, it was discovered that parameters of the sequence of short push pulses can be adapted to form two shear waves (referred to as a push shear wave and a release shear wave) that are separated in time, with the push shear wave corresponding to the onset of the collective push (i.e., the first short push pulse in the set) and the release shear wave corresponding to the end of the collective push (i.e., the last short push pulse in the set). Propagation of the first, push shear wave propels the tissue away from the transducer, while propagation of the second, release shear wave moves the tissue towards the transducer.

A single long push pulse with duration longer than about 1 millisecond is sufficient to produce such push and release shear waves. However, the use of a single long push pulse would require a specifically-designed transmit circuit, or the use of transmit voltage reduced to avoid power droop for such a long transmit duration. In contradistinction, the total duration of a collective push including a sequence of many short push pulses can easily reach many milliseconds without causing power droop, making this an ideal method to produce pairs of push and release shear waves. The use of both the first and the second shear waves for determination of the tissue mechanical properties not only increases the accuracy and precision of such determination, but also facilitates characterization of a non-linearity of the material of the subject because the push and release shear wave have opposite polarity.

Figure 4:
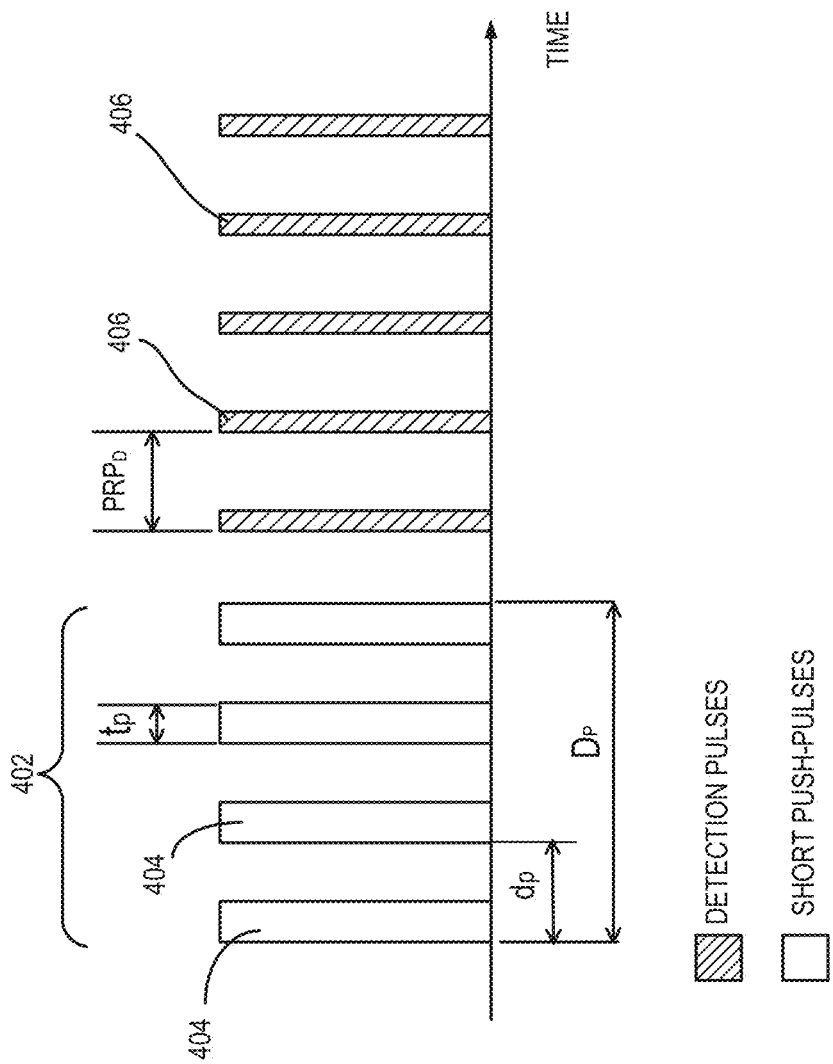
FIG. 4 is a time diagram illustrating, according to an embodiment of the invention, a sequence of short-duration push pulses followed by detection pulses.

In reference to FIG. 4, an example of a sequence 402 of short push-pulses shown, according to an embodiment of the invention, to substitute a long-duration push-pulse 202 of FIG. 2, for example. Each of the short push-pulses 404 in the sequence 402 has a corresponding duration that is shorter than the duration $T_P$ of the substituted long-duration push-pulse 202. For example, a duration $t_P$ of a short push-pulse 404 can be chosen to be on the order of several to tens of microseconds as compared to the duration $T_P$ of about hundreds of milliseconds used in a configuration corresponding to FIG. 2. The collective effect of the short pulses 404 of the sequence 402 amounts to generating a motion in tissue with a large amplitude (exceeding the amplitude of the tissue motion caused by the single long-duration push-pulse 202 of FIG. 2, as formed and measured under otherwise the same conditions) for reliable shear wave detection and subsequent calculation of tissue mechanical properties.

Figure 5A:
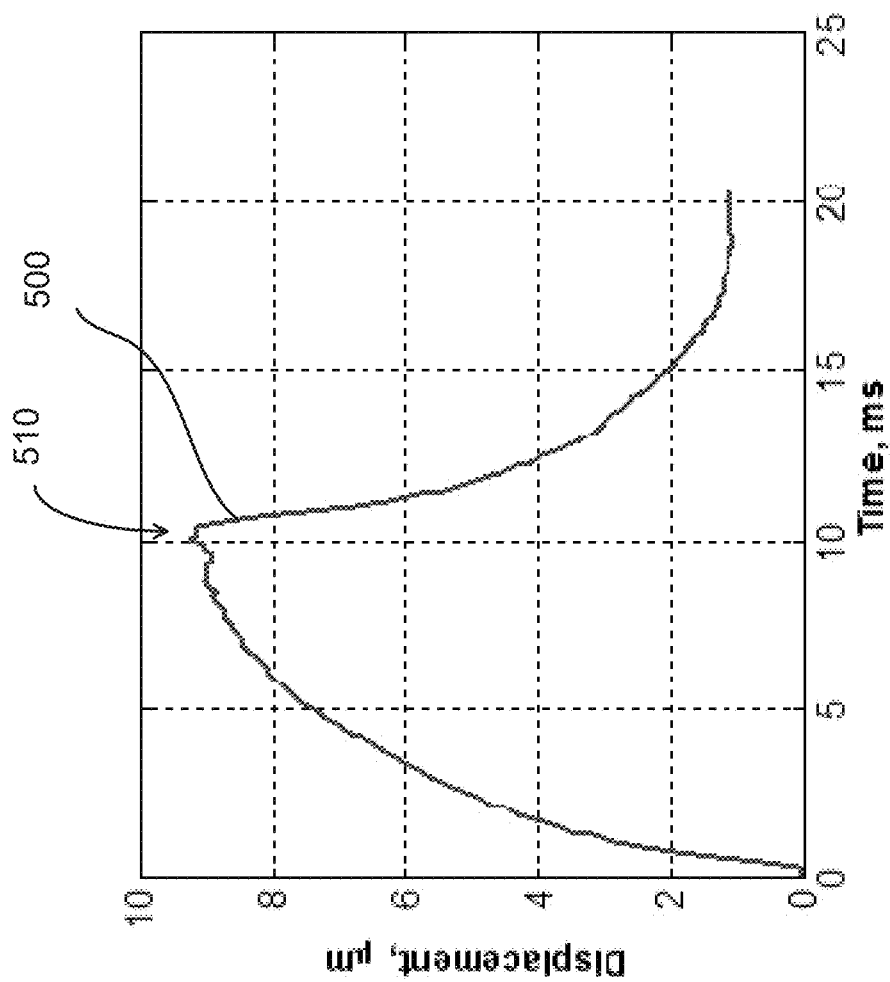
FIG. 5A is a graph of displacement of the medium at the push origin (push focus) caused by the sequence of short-duration push pulses of FIG. 4.

FIG. 5A, for example, illustrates motion 500 produced in a tissue-mimicking material by a sequence of 64 short push-pulses (similar to the sequence 402 of FIG. 4) with the following characteristics: $t_p$ of about 3 microseconds, $PRF_P$ (i.e., $1/d_p$) of about 6.25 kHz, and $D_P$ of about 10 ms. Most ultrasound scanners should be able to produce the push pulses with characteristics used in this experiment because the $t_p$ and $PRF_P$ used here are similar to the pulses used in Doppler mode. Motion of the push origin (focus of the push-beam in this case) was continued to be monitored for about 10 ms after termination of the collective push composed of 64 short push-pulses. As can be seen from FIG. 5A, the displacement of a tissue element increases during about 10 ms after the collective push is switched on a time t=0, and decreases after the collective push is switched off (at t~$D_P$).

Figure 5B:
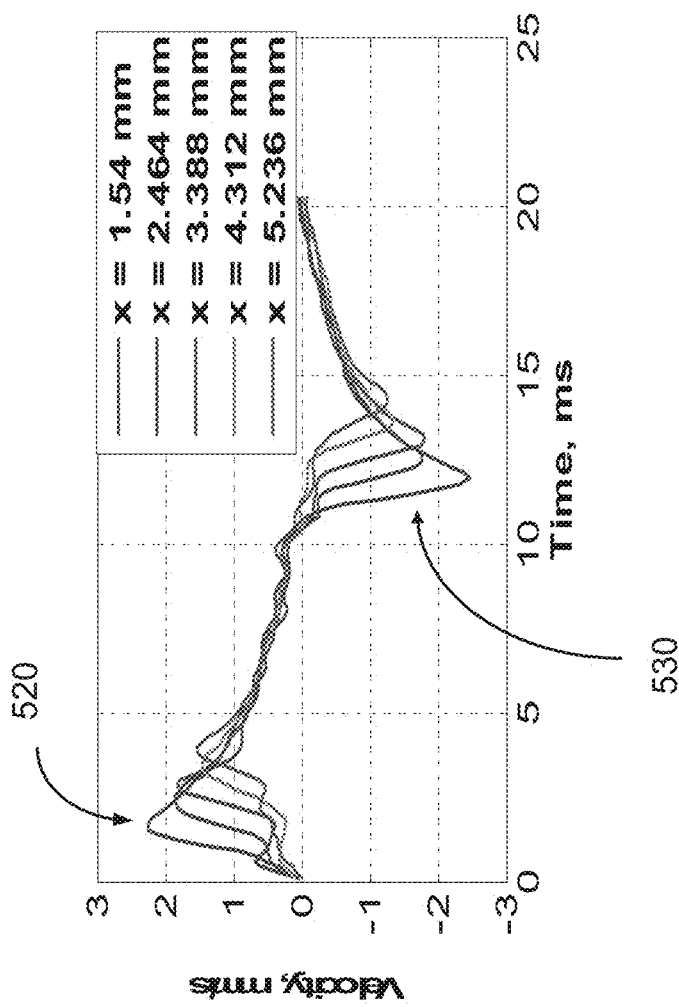
FIG. 5B is a plot demonstrating velocity of medium particles at different lateral positions from the push origin, caused by the push and release shear waves of an embodiment of the invention.

Motion 500 at push origin produces first and second shear waves propagating outwardly that can be used to evaluate tissue mechanical properties. FIG. 5B demonstrates shear wave motions (particle velocity which is the time derivative of displacement) at different lateral positions x with respect to the push origin, which contains a push wave 520 and a release wave 530. The push shear wave is caused by the rising onset of the collective push pulse (corresponding to the rising portion of 500). When the sequence of ultrasound pulses 402 applied to the subject, is over (or turned off), the medium at the push origin displaced by the sequence 402 returns to its equilibrium position, thereby generating a second shear wave referred to herein as the release wave. The release wave, just like the preceding push wave, displaces the elements of the subject medium upon its propagation through it. It is understood, however, that due to the nature of formation of the release wave and as compared to the push wave, the displacement of the elements of the subject medium in response to the release wave occurs in the direction opposite to that corresponding to the displacement of the elements of the subject medium in response to the push wave.

In further reference to FIG. 5B and referring again to FIG. 4, parameters of short-duration push pulses of the sequence 402 can be appropriately adjusted to produce shear waves with differing characteristics. For example, the use of larger $t_p$, smaller $d_p$, or larger $D_p$ (corresponding to a greater number of pulses in the sequence 402) increases the amplitude of the resulting shear wave. Generally, $d_p$ is preferably small enough to allow efficient build-up of the tissue motion between sequential short duration push pulses (because tissue displaced by the previous push will move back to original position before the next push if $d_p$ is too large). Increase of the value of $D_p$ leads to the increase of temporal (and, therefore, spatial) separation between the push and release shear waves. Assuming a shear wave speed of 1.5 m/s in the chosen subject medium, a $D_p$ of about 10 ms leads to the release wave following behind the push wave by about 15 mm. Moreover, in a non-linear material, the push wave and the release wave will have different characteristics because material response depends on the polarity of shear wave. Accordingly, characterization of the medium of propagation with the use of both the push and release waves may be tailored to the characterization of the non-linearity of such medium.

Figure 6A:
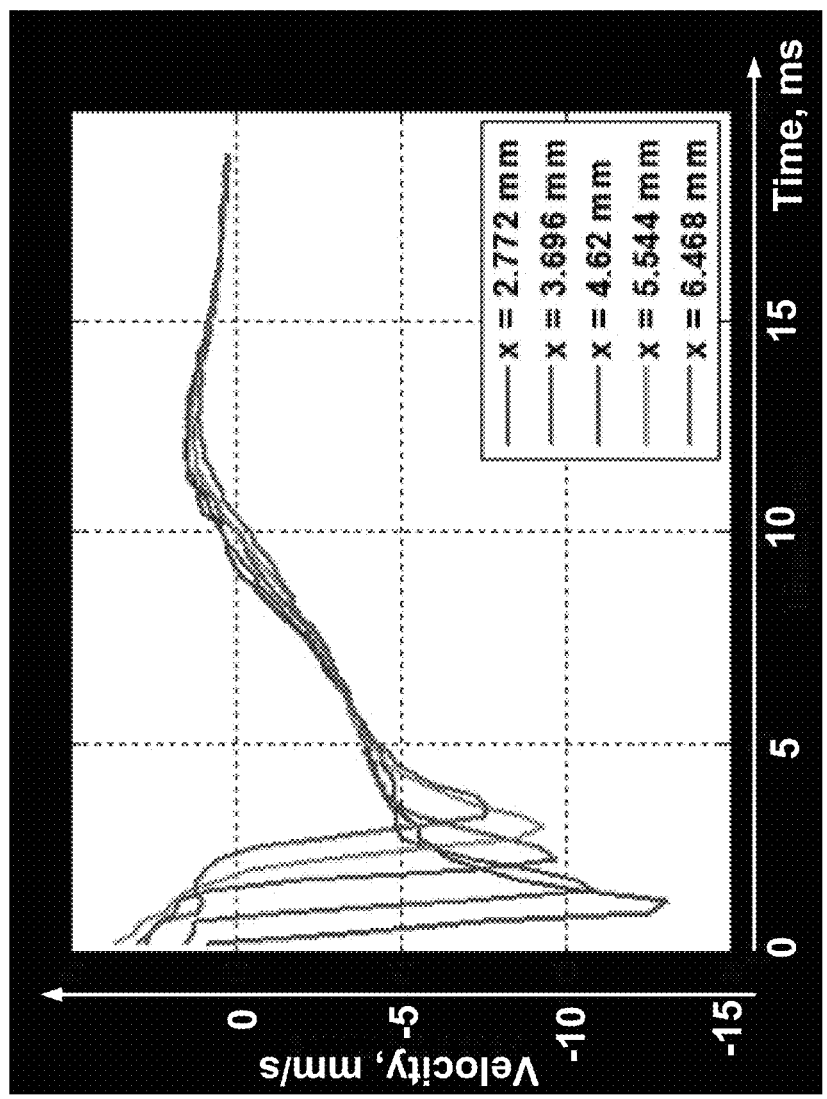
FIG. 6A is a graph illustrating velocity of medium particles at different lateral position from the push origin, caused by the release shear wave.
Figure 6B:
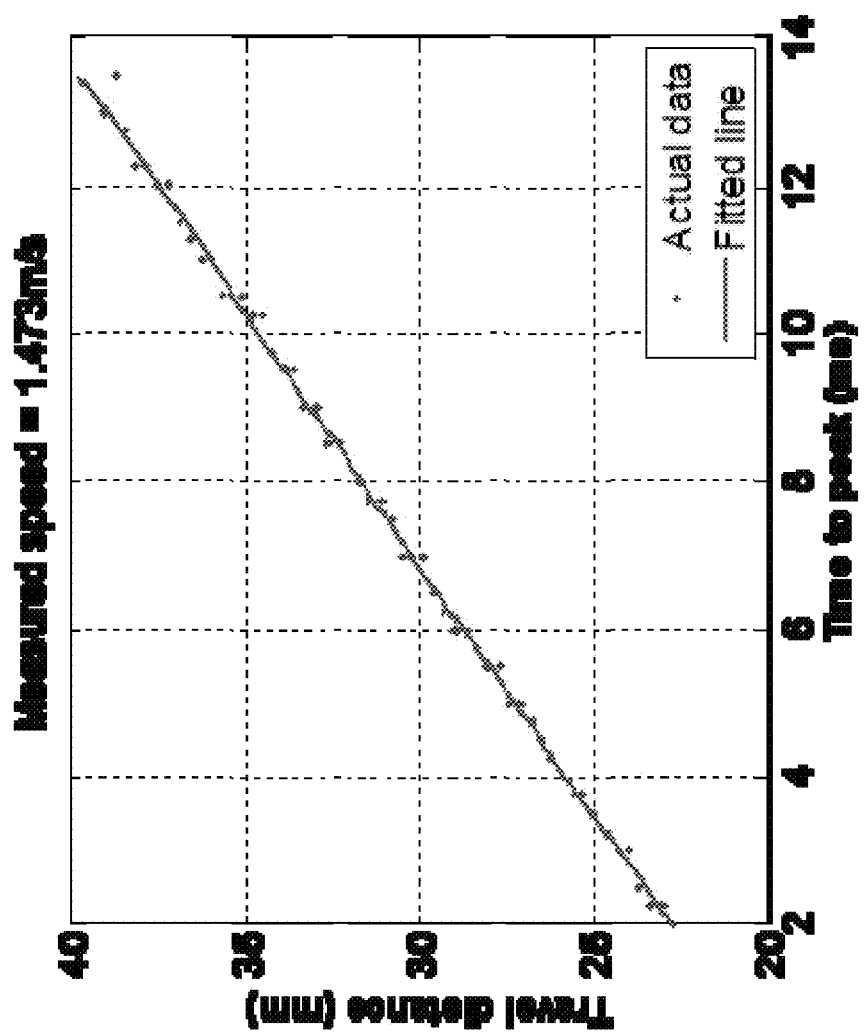
FIG. 6B is a plot of time-to peak regressing of the speed of the release shear wave corresponding to FIG. 6A.

FIG. 6A is a graph of the medium-particle velocity in the same test material corresponding to FIG. 5B, but with different push parameters. Here, $t_p$ is about 6.4 µs, $d_p$ is about 40 µs, and Dp is about 5 ms). In the experiment corresponding to FIG. 6A, the shear wave detection was performed after the termination of the collective push pulse. Accordingly, the push wave has already passed and only the release shear wave is shown here. The motion amplitude of the particle oscillation is larger as compared to that of FIG. 5B. The time-to-peak regression corresponding to the release shear wave of FIG. 6A is shown in FIG. 6B, illustrating a shear wave speed of about 1.47 m/s. An independent measurement of the shear wave speed in the same material carried out by MRE (Magnetic Resonance Elastography) delivered the value of 1.47±0.02 m/s.

Another benefit provided by the embodiment of the method discussed above is that the duration of each of the short push pulses may be at least an order of magnitude shorter than that of a long duration push-pulse of FIG. 2, which causes minimization of the power droop of the ultrasound scanner. It is noted that ultrasound scanners are typically designed to transmit very short pulses of a few microseconds for B-mode imaging. Thus, low-to-mid-end scanners cannot provide enough power to transmit a longer duration push beam and, as a result, the amplitude of the push beam substantially droops if the push duration is longer than a certain duration threshold. Power droop can lead to small magnitudes of tissue motion and poor shear wave measurements.

Characteristics of the push and release shear waves and motion of the subject tissue can be determined, for example, with the use of a two-dimensional Fast Fourier Transform (FFT) technique, resulting in parameters of dispersion of the shear waves propagating through the tissue. Alternatively, the dispersion of the shear wave velocity can be calculated via phase regression and application of a one-dimensional FFT to each of the time records corresponding to elements of tissue.

Figure 7A:
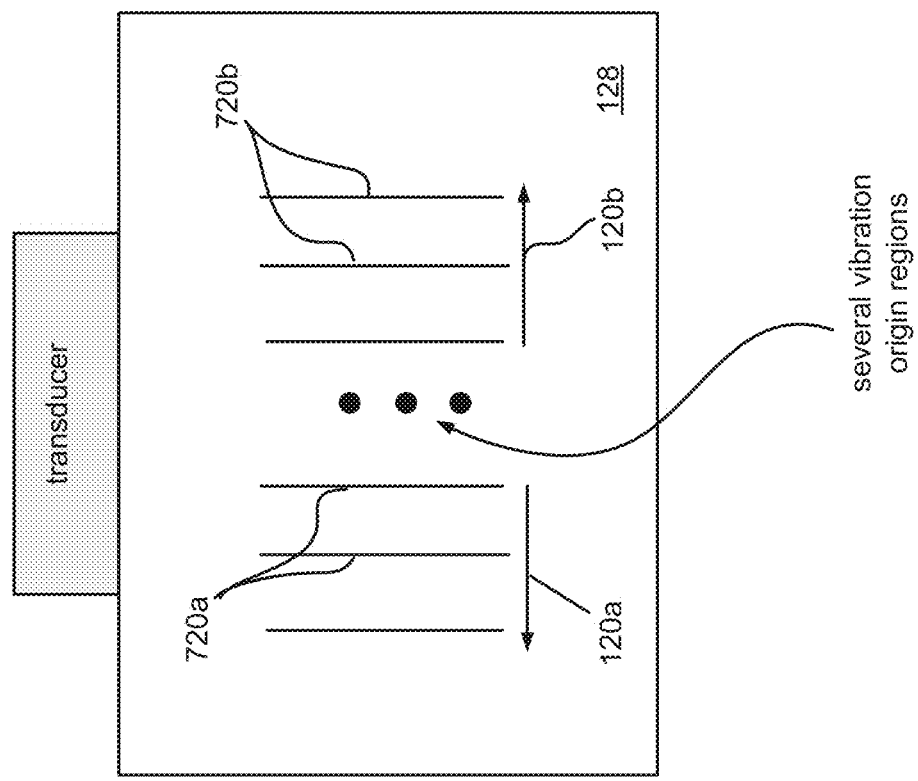

In producing shear waves with a set of short push pulses according to an embodiment of the invention, various push schemes can be implemented. For example, the push scheme with all short push pulses focused at a single focal region (as shown in FIG. 1) can be used to generate shear waves with relatively short axial extent. Alternatively or in addition, the push scheme can be modified, as shown in FIGS. 7A through 7C to cycle the push pulses to different multiple tissue regions to generate shear waves having different spatial characteristics. For example, the use of multiple push origin regions along different depths of the tissue, as shown in FIG. 7A, can facilitate creation of shear waves 720a, 720b of axial extent that exceeds the axial extent of the waves 124a, 124b of FIG. 1. Push origin regions arranged in a fashion similar to that of FIG. 7B can produce shear waves for SMURF application (see, for example, *IEEE Trans. Ultrasonic, Ferroelectrics, and Frequency Control.* 58, 1344-54, 2011). Push origin regions arranged in a fashion similar to that of FIG. 7C (along a line at angle to the vertical axis representing the depth of tissue 128) can facilitate formation of shear waves at an oblique angle, which can be used for shear wave compounding image (see, for example, *IEEE Transactions on Ultrasonics, Ferroelectrics, and Frequency Control*, vol. 51, No. 4, 2004). Generally, a push scheme and a generation of push and release shear waves can utilize unfocused ultrasound beams, but in one implementation such beams may be focused thereby making corresponding push origin regions substantially coincide with focal regions of the push beams. In a specific implementation, a created push origin region has such small spatial extent as to substantially turn into a push origin point.

Shear waves generated by various combinations of push schemes can be used for time-to-peak shear wave propagation group velocity measurements, or frequency dependent shear wave propagation speed dispersion analysis, as taught above. They can also be used for SMURF measurements and Direct Inversion of the wave equation for 2D storage and loss modulus reconstruction. The push and detection pulses can also be spaced unevenly in time. If needed, detection pulses can be interleaved with the push pulses to monitor tissue motion during the collective push phase. The detection pulses can be focused as in traditional ultrasound scanner or unfocused plane wave as in plane wave imaging. In addition to shear wave speed, change of shear wave amplitude during propagation can also be analyzed to evaluate shear wave attenuation and tissue viscoelasticity. Tissue properties evaluated from the propagation of the push or release shear wave can be used to calibrate the model-free storage and loss modulus evaluated at the push origin during a creep test.

Embodiments of the present invention also provide a method for determination of velocity and attenuation of a shear wave. Current methods for analyzing the shear wave propagation are designed to suit traditional ultrasound scanners which image one line from one transmit-receive event. Typically, shear waves are detected at only a few positions along the shear wave propagation path, and detection at each position is repeated at a Pulse Repetition Frequency (PRF) of several kilohertz for tens of milliseconds. Therefore, the measured time-space shear wave data typically composes of only a few spatial points along the shear wave propagation path, but a lot more time points. Accordingly, currently used methods for analyzing shear waves require sampling of the shear wave in time at high PRF for relatively long time (typically tens of milliseconds). As discussed above, such relatively long detection period may limit the use of such methods in detecting rapid changes of tissue elasticity. In addition, long detection period makes shear wave signal susceptible to interference from physiological tissue motion (for example, gross motion of the beating heart).

With "plane wave imaging", it is possible to detect the shear wave propagation at many lateral locations along the shear wave propagation path with just two transmit-receive events (echoes from these two events are used to calculate tissue motion between the events). The time interval between the two events is at the order of 100 microseconds, which is very fast compared to the propagation of the shear wave (typically only a few meters per second). Therefore, the use of "plane wave imaging" essentially enables a snapshot of spatial distribution of shear wave at an instant of time. Embodiments of the present invention take advantage of this and provide a method adapted for analyses of the time-space shear wave data with many spatial points but only a few time points. This is achieved by analyzing the spatial distribution of one or more shear wave front. As a result, measurements of tissue properties with the use of the proposed method only requires detection of a shear wave during a very short time period. This is beneficial for measuring tissues with rapidly changing properties and for minimizing interference of physiological motion.

Figure 8A:
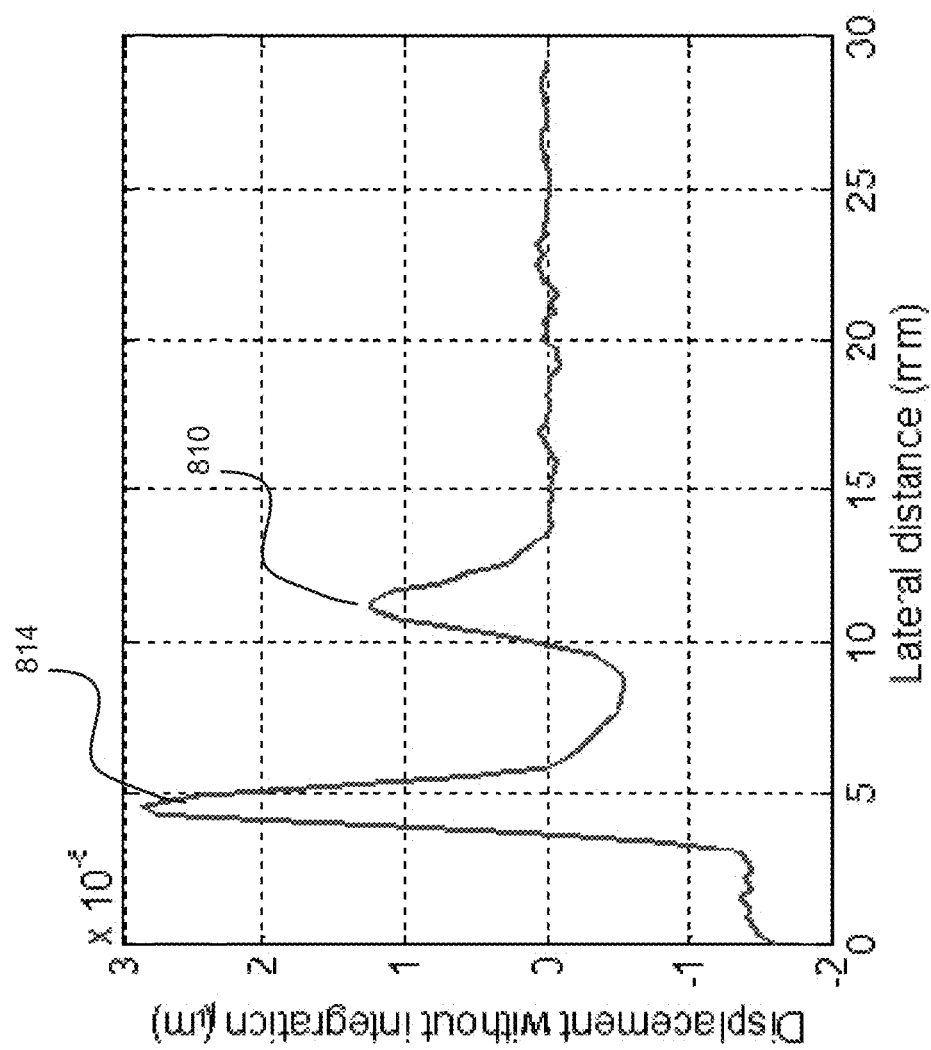
FIG. 8A is a plot representing snapshots of the shear wave fronts from 2 push beams separated in time for 5 milliseconds but focused at the same location at the tissue.

In one embodiment, the group velocity of the shear wave propagation is calculated from only a single snapshot of the shear wave spatial distribution. By way of example, FIG. 8A is a plot showing a snapshot of two shear wave fronts produced by two push beams separated in time by $\Delta t$=5 milliseconds but focused at the substantially same location in a tissue-mimicking material such as gelatin or agar. The plot of FIG. 8A reveals the spatial distribution of the shear wave at an instant of time. The peak 810 at about 12 mm distance from the origin is the shear wave front produced by the first push pulse and the peak 814 at about 4 mm is the shear wave front produced by the second push pulse. The group velocity of the shear wave propagation in the material is calculated by dividing the spatial distance $\Delta r$ between the two peaks by $\Delta t$. In this example, $\Delta r$=6.8 mm and $\Delta t$=5 ms, leading to a group velocity of about 1.36 m/s. Independent measurements of the group velocity of this test material by other methods indicate the close value of 1.38 m/s.

Figure 8B:
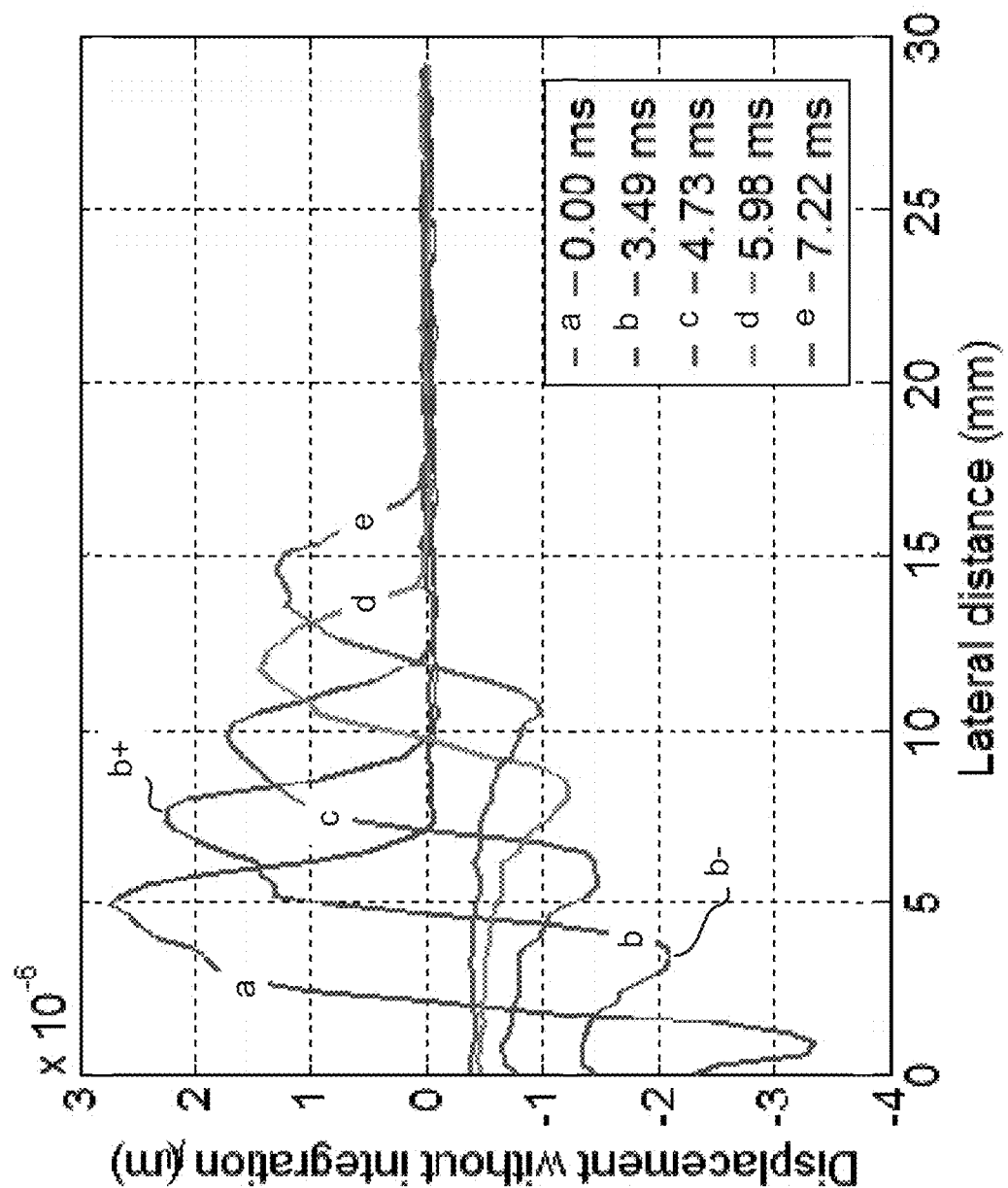
FIG. 8B is a plot representing snapshots of the positive and negative shear wave fronts produced by push and release shear waves formed by a sequence of multiple short push pulses according to an embodiment of FIG. 4.

In another example, FIG. 8B shows plots a through e representing a few snapshots of the shear waves produced by a sequence of short push pulses 9 such as the sequence 402 of FIG. 4) focused at substantially the same location (corresponding to a point at 0 mm of FIG. 8B) in another tissue mimicking material with different shear wave speed. At each instant of time, the shear wave has a positive peak (shown, in the case of plot b, as b+) corresponding to a push shear wave and a negative peak (shown, in the case of plot b, as b−) corresponding to the release shear wave. The duration of the collective push is $D_p$ of about 2 milliseconds ($\Delta t$) and the shear wave group velocity can be calculated from the spatial distance between the push and release shear waves ($\Delta r$) as: $c_S = \Delta r/\Delta t$. Only one snapshot is required to measure the group velocity. The averaged group velocity calculated from several snapshots in FIG. 8B is 1.95±0.18 m/s. This result agrees with independent measurements of the group velocity of this test material by other methods which give about 1.90 m/s.

Figure 9A:
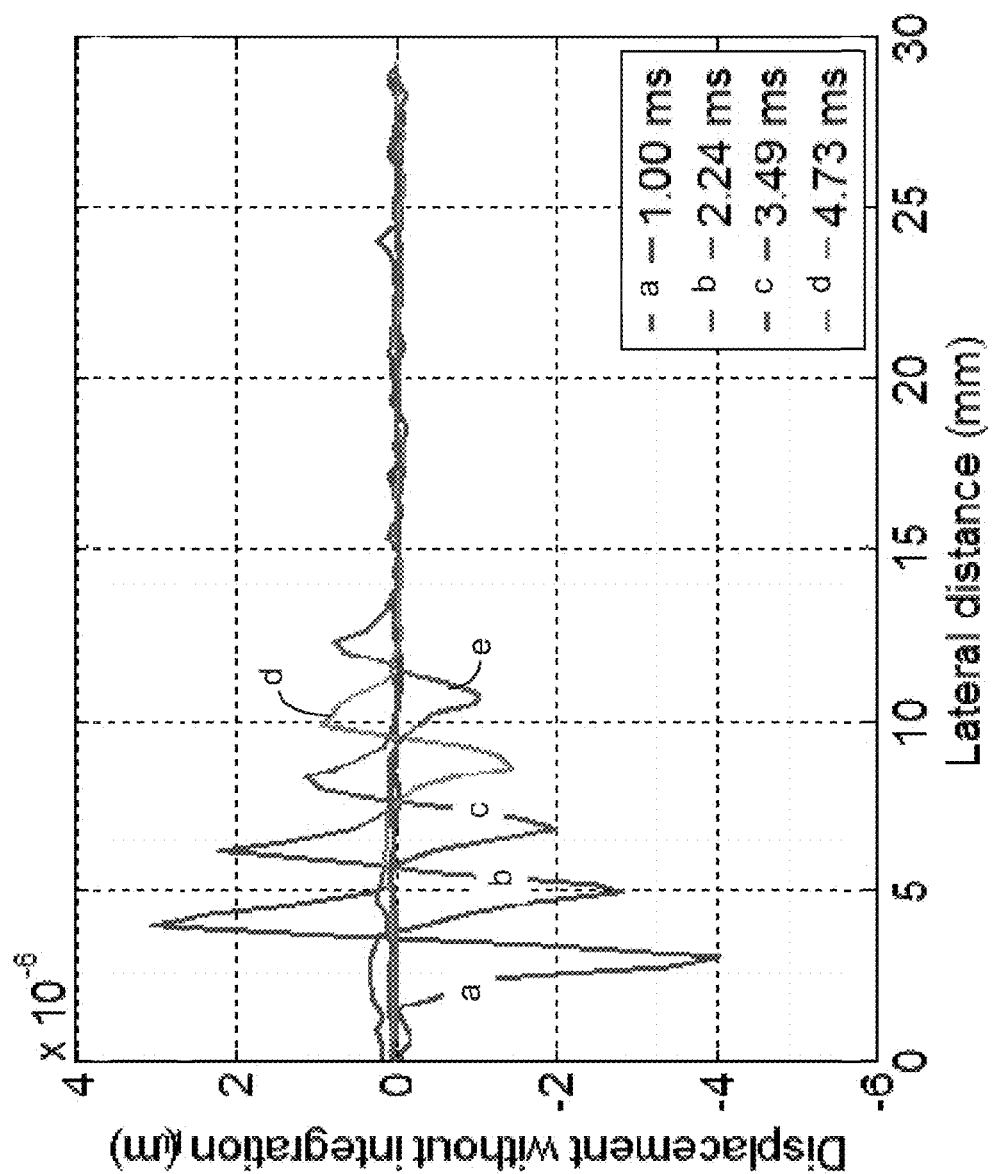
FIG. 9A is a plot representing snapshots of the tissue particle acceleration due to propagation of shear wave, at several moments of time.
Figure 9B:
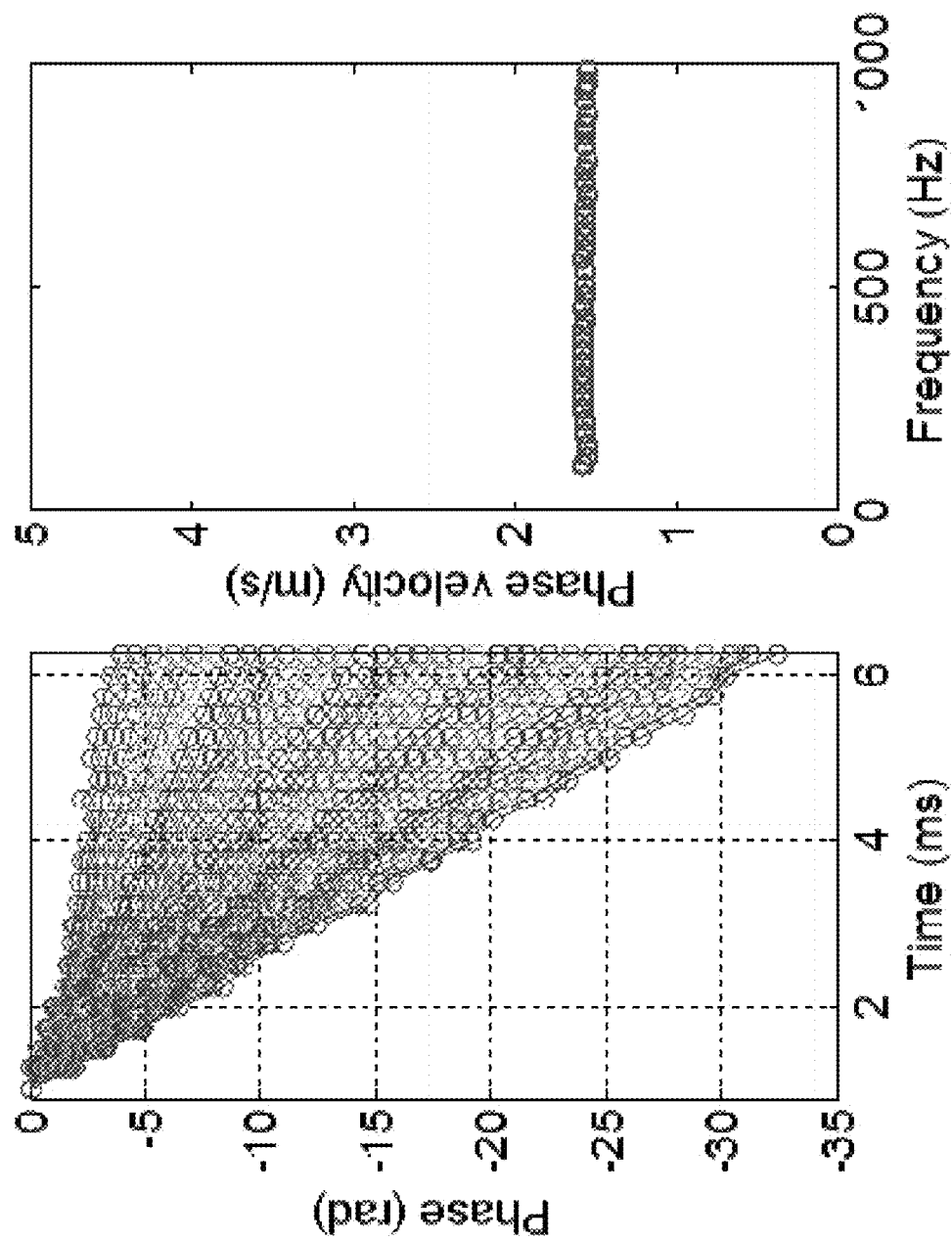
FIG. 9B is a plot showing linear regression of phases versus time (left panel) and the calculated propagation phase velocity (right panel).

In another embodiment, the shear wave propagation phase velocity can be calculated from the spatial shape of one shear wave front at two or more time instances. For example, FIG. 9A shows plots representing snapshots taken at a few time instants during the propagation of a shear wave produced by a single continuous push beam in a tissue mimicking material. The location of the focus of the push beam is denoted as a lateral distance of 0 mm. Each of the curves a through e curve of FIG. 9A is a spatial profile, which can be Fourier transformed to the spatial frequency domain (k domain). The phase of a given spatial frequency k can be obtained for each of different time instances, as shown in FIG. 9B. The phase change ΔØ decreases linearly with time interval Δt between the snapshots with a slope s=ΔØ/Δt. The shear wave phase velocity at spatial frequency k can be calculated as $$c_s(k) = \frac{\Delta\phi}{\Delta t \times 2\pi k}.$$

This is also the shear wave phase velocity at $$\text{temporal frequency} = k \times c_s = \frac{\Delta\phi}{2\pi\Delta t}.$$

The calculation requires at least 2 snapshots of the shear wave propagation. If more snapshots are available, the slope s can be obtained through linear regression. This process can be repeated to calculate shear wave phase velocity at other temporal frequencies. The right image panel of FIG. 9B shows the phase velocity calculated in the frequency range from about 0 Hz to about 1000 Hz as described above. This result agrees with independent measurements by other methods which results in a constant phase velocity of about 1.5 m/s for this tissue mimicking material in the same frequency range.

Similarly, an amplitude of a shear wave at a given spatial frequency can be calculated for different snapshots of FIG. 9A, and plotted as a function of shear wave propagation distance R, where $$R = \frac{\Delta\phi}{2\pi k}.$$

Such calculation provides an opportunity to estimate the shear wave attenuation parameter at a given spatial frequency (and therefore a given temporal frequency). Optionally, a correction for geometric attenuation (arising due to the spreading of the shear wave energy over larger areas as the shear wave produced by the ultrasound push beam propagates outwards from the push origin) should be performed. After properly correcting for geometric attenuation, the shear wave attenuation due to material damping and/or viscosity can be estimated by fitting the amplitude-distance curve.

A single shear wave front is used in the above example, and therefore two or more snapshots are required to calculate phase velocity and attenuation. Two or more shear wave fronts separated in both time and space can also be produced as taught in FIG. 8A and FIG. 8B. In such cases, only one snapshot is required to calculate the phase velocity and attenuation by analyzing the change of the spatial distribution of these two shear wave fronts, which travels different distance Δr and time Δt.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for characterizing a subject with an ultrasound system, the method comprising:
applying a set of short ultrasound push pulses to a first push origin at the subject;
detecting with the ultrasound system, after the set of short ultrasound push pulses has been completely applied, ultrasound echo energy representing first and second temporally resolved shear waves propagating through the subject from the first push origin; and
calculating a mechanical property of the subject using echo data representing detected ultrasound echo energy,
wherein the first and second temporally resolved shear waves have opposite polarities.

2. A method according to claim 1, wherein the calculating a mechanical property includes calculating at least one of propagation velocity and attenuation of a shear wave through the subject.

3. A method according to claim 1, wherein the calculating a mechanical property includes calculating at least one of a shear storage modulus, a shear loss modulus, and a shear viscosity.

4. A method according to claim 1, further comprising applying a set of short ultrasound push pulses to a second push origin at the subject,
wherein applying a short ultrasound push pulse to the to the first push origin is alternated with applying a short ultrasound pulse to the second push origin to form a sequence of short ultrasound pulses alternately applied to the first and second push origins.

5. A method according to claim 1, further comprising applying a set of short ultrasound push pulses to a second push origin at the subject before said detecting.

6. A method according to claim 1, wherein said applying includes applying a set of pulses duration of each of which is several microseconds.

7. A method according to claim 1, wherein said calculating a mechanical property of the subject includes determining a motion of a tissue of the subject occurring with a first amplitude that exceeds a second amplitude, the second amplitude being an amplitude of a motion of said tissue caused by applying a single long push pulse to said first origin, said single long push pulse having a duration equal to a duration of said set of short ultrasound pulses, said single long push pulse having an amplitude equal to an amplitude of a single short ultrasound push pulse from said set.

8. A method according to claim 1, wherein said second temporally-resolved shear wave having originated later than the first temporally resolved shear wave.

9. A method according to claim 1, further comprising determining at least one of a non-linearity of a material of the subject and a dispersion of a shear-wave velocity using said echo data.

10. A method for characterizing a subject with an ultrasound system, the method comprising:
detecting ultrasound energy reflected from the subject, said ultrasound energy representing first and second shear waves formed in the subject in response to irradiation with an ultrasound beam produced by the ultrasound system, said first and second shear waves being spatially separated and characterized by opposite polarities;
determining spatial distributions of said first and second shear waves at one or more moments of time; and
calculating a mechanical property of the subject using data representing determined spatial distributions.

11. A method according to claim 10, wherein said determining spatial distributions includes determining a distance between first and second shear wave fronts at at least one moment of time, and wherein said calculating includes calculating a group velocity of propagation of a shear wave.

12. A method according to claim 11, wherein said determining a distance includes determining a distance between a front of the first shear wave and a front of the second shear wave.

13. A method according to claim 10, wherein said determining spatial distributions includes determining a phase of a shear wave at a given spatial frequency at at least one moment of time, and wherein said calculating includes calculating a phase velocity of propagation of a shear wave at a first temporal frequency.

14. A method according to claim 10, wherein said determining spatial distributions includes determining an amplitude of a shear wave at a chosen spatial frequency at at least one moment of time, and wherein said calculating includes calculating a parameter representing attenuation of a shear wave at a single temporal frequency.

15. A method according to claim 10, wherein said determining spatial distributions includes determining at least one of a speed and attenuation of a shear wave upon propagation through the subject.

16. A method according to claim 10, wherein said calculating a mechanical property includes calculating at least one of a shear storage modulus, a shear loss modulus, and a shear viscosity.

17. A method according to claim 10, wherein said calculating a mechanical property of the subject includes calculating said mechanical property based on non-linear response of said subject to changing parameters of said first and second shear waves.

18. A method according to claim 10, further comprising determining at least one of a non-linearity of a material of the subject and a dispersion of a shear-wave velocity using said data representing determined spatial distributions.

* * * * *